(12) United States Patent
Takeda et al.

(10) Patent No.: US 7,097,977 B1
(45) Date of Patent: Aug. 29, 2006

(54) TARGET OF ANTICANCER AGENT

(75) Inventors: Shunichi Takeda, Kyoto (JP); Minoru Takata, Kyoto (JP)

(73) Assignee: Japan Science and Technology Corporation, Kawaguchi (JP)

( * ) Notice: Subject to any disclaimer, the term of this patent is extended or adjusted under 35 U.S.C. 154(b) by 460 days.

(21) Appl. No.: 10/332,858

(22) PCT Filed: Jul. 14, 2000

(86) PCT No.: PCT/JP00/04739

§ 371 (c)(1),
(2), (4) Date: Jan. 14, 2003

(87) PCT Pub. No.: WO02/06481

PCT Pub. Date: Jan. 24, 2002

(51) Int. Cl.
*C12Q 1/68* (2006.01)
*C12N 5/00* (2006.01)
*C12N 5/02* (2006.01)
*C07H 21/02* (2006.01)
*C07H 21/04* (2006.01)

(52) U.S. Cl. .................... 435/6; 435/325; 536/23.1

(58) Field of Classification Search ............... None
See application file for complete search history.

(56) References Cited

FOREIGN PATENT DOCUMENTS

| WO | WO 98/11214 A | 3/1998 |
| WO | WO 95/25429 A | 11/1999 |
| WO | WO 99/57144 A | 11/1999 |

OTHER PUBLICATIONS

Kanaar et al; Trends in Cell Biology, vol. 8, pp. 483-489, 1998.*
Yamada et al; The Journal of Biological Chemistry, vol. 279, pp. 23250-23254, 2004.*
Thacker, J; Cancer Letters, vol. 219, pp. 125-135, 2005.*
Yonetani et al; Nucleic Acids Research, vol. 33, pp. 4544-4552, 2005.*
Miller et al; Nucleic Acids Research, vol. 32, pp. 169-178, 2004.*
Shiu et al, Molecular and Cellular biology, 1999, vol. 19, pp. 8686-8693.*
Havre et al; Cancer Research, vol. 58, pp. 4733-4739, 1998.*
Shoenmakers et al; Cancer Research, vol. 59, pp. 19-23, 1998.*
Takata et al (Molecular and Cellular Biology, Sep. 2000, vol. 20, pp. 6476-6482).*
James E. Haber; Trends Biochem. Sci., vol. 24, pp. 271-275, 1999.
Akira Shinohara et al.; Nature Genetics, vol. 4, pp. 239-243, 1993.
Olga Bezzubova et al.; Cell, vol. 89, pp. 185-193, 1997.
Jeroen Essers et al.; Cell, vol. 89, pp. 195-204, 1997.
Ronald Kanaar et al.; Trends in Cell Biology, vol. 8, pp. 483-489, 1998.
Eiichiro Sonoda et al.; The EMBO Journal, vol. 17, No. 2, pp. 598-608, 1998.
Roger D. Johnson et al.; Nature, vol. 401, pp. 397-399, 1999.
Andrew J. Pierce et al.; Genes & Development, vol. 13, pp. 2633-2638, 1999.
Manjit K. Dosanjh et al.; Nucleic Acids Research, vol. 26, No. 5, pp. 1179-1184, 1998.
Nan Liu et al.; Molecular Cell, vol. 1, pp. 783-793, 1998.
Patrick Sung; Genes & Development, vol. 11, pp. 1111-1121, 1997.
Nge Cheong et al.; Mutation Research, DNA Repair, vol. 314, pp. 77-85, 1994.
Minoru Takata et al.; The EMBO Journal, vol. 17, No. 18, pp. 5497-5508, 1998.
Eiichiro Sonoda et al.; Molecular and Cellular Biology, vol. 19, pp. 5166-5169, 1999.
Douglas K. Bishop et al.; The Journal of Biological Chemistry, vol. 273, No. 34, pp. 21482-21488, 1998.
John Thacker, Trends Genet. vol. 15, pp. 166-168, 1999.
Minoru Takata et al.; Molecular and Cellular Biology, vol. 20, pp. 6476-6482, 2000.
Minoru Takata et al.; Molecular and Cellular Biology, vol. 21, pp. 2858-2866, 2001.
Hillier, LD, et al. Genome Res. vol. 6, No. 9, pp. 807-828, 1996.
Alabala, JS, et al. Genomics, vol. 46, No. 3, pp. 476-479, 1997.
Rice, MC, et al. Proc. Natl. Acad. Sci. USA, vol. 94, No. 14, pp. 7417-7422, 1997.
Cartwright, R, et al. Nucleic Acids Res, vol. 26, No. 7, pp. 1653-1659, 1998.
Adams, MD, et al. Nat. Genet., vol. 4, No. 4, pp. 373-380, 1993.

* cited by examiner

*Primary Examiner*—Jehanne Sitton
(74) *Attorney, Agent, or Firm*—Birch, Stewart, Kolasch & Birch, LLP

(57) ABSTRACT

To provide a mutant Rad51 paralog gene, wherein a protein encoded thereby shows an activity for enhancing sensitivity of a cell to a DNA-damaging factor; a mutant Rad51 paralog peptide showing the activity; a transformed cell having the gene; a screening method for a drug having a DNA-damaging action, comprising contacting a test substance with the transformed cell, and evaluating a response of the cell; and a screening method for a controlling agent for DNA repair, comprising contacting a test substance with a transformed cell having the Rad51 paralog gene, and evaluating a homologous recombination repair capacity. According to the present invention, there is enabled a screening of a novel anticancer agent which allows a more efficient therapy for a cancer, wherein the agent is an agent capable of enhancing the sensitivity of a cell to an anticancer agent comprising a DNA-damaging factor or an agent having a DNA-damaging action.

5 Claims, 4 Drawing Sheets

SEQUENCE LISTING

<160> NUMBER OF SEQ ID NOS: 6

<210> SEQ ID NO 1
<211> LENGTH: 1764
<212> TYPE: DNA
<213> ORGANISM: Homo sapiens
<220> FEATURE:
<221> NAME/KEY: 5'UTR
<222> LOCATION: (1)..(54)
<220> FEATURE:
<221> NAME/KEY: CDS
<222> LOCATION: (55)..(1107)
<220> FEATURE:
<221> NAME/KEY: 3'UTR
<222> LOCATION: (1108)..(1764)
<220> FEATURE:
<221> NAME/KEY: polyA_signal
<222> LOCATION: (1727)..(1732)

<400> SEQUENCE: 1

```
gggaaactgt gtaaagggtg gggaaacttg aaagttggat gctgcagacc cggc atg      57
                                                              Met
                                                              1 ggt agc aag aaa cta aaa cga gtg ggt tta tca caa gag ctg tgt gac     105
Gly Ser Lys Lys Leu Lys Arg Val Gly Leu Ser Gln Glu Leu Cys Asp
        5                  10                  15 cgt ctg agt aga cat cag atc ctt acc tgt cag gac ttt tta tgt ctt     153
Arg Leu Ser Arg His Gln Ile Leu Thr Cys Gln Asp Phe Leu Cys Leu
     20                  25                  30 tcc cca ctg gag ctt atg aag gtg act ggt ctg agt tat cga ggt gtc     201
Ser Pro Leu Glu Leu Met Lys Val Thr Gly Leu Ser Tyr Arg Gly Val
 35                  40                  45 cat gaa ctt cta tgt atg gtc agc agg gcc tgt gcc cca aag atg caa     249
His Glu Leu Leu Cys Met Val Ser Arg Ala Cys Ala Pro Lys Met Gln
 50              55                  60                  65 acg gct tat ggg ata aaa gca caa agg tct gct gat ttc tca cca gca     297
Thr Ala Tyr Gly Ile Lys Ala Gln Arg Ser Ala Asp Phe Ser Pro Ala
                 70                  75                  80 ttc tta tct act acc ctt tct gct ttg gac gaa gcc ctg cat ggt ggt     345
Phe Leu Ser Thr Thr Leu Ser Ala Leu Asp Glu Ala Leu His Gly Gly
                 85                  90                  95 gtg gct tgt gga tcc ctc aca gag att aca ggt cca cca ggt tgt gga     393
Val Ala Cys Gly Ser Leu Thr Glu Ile Thr Gly Pro Pro Gly Cys Gly
            100                 105                 110 aaa act cag ttt tgt ata atg atg agc att ttg gct aca tta ccc acc     441
Lys Thr Gln Phe Cys Ile Met Met Ser Ile Leu Ala Thr Leu Pro Thr
        115                 120                 125 aac atg gga gga tta gaa gga gct gtg gtg tac att gac aca gag tct     489
Asn Met Gly Gly Leu Glu Gly Ala Val Val Tyr Ile Asp Thr Glu Ser
```

```
              130                 135                 140                 145
gca ttt agt gct gaa aga ctg gtt gaa ata gca gaa tcc cgt ttt ccc              537
Ala Phe Ser Ala Glu Arg Leu Val Glu Ile Ala Glu Ser Arg Phe Pro
                    150                 155                 160 aga tat ttt aac act gaa gaa aag tta ctt ttg aca agt agt aaa gtt              585
Arg Tyr Phe Asn Thr Glu Glu Lys Leu Leu Leu Thr Ser Ser Lys Val
                165                 170                 175 cat ctt tat cgg gaa ctc acc tgt gat gaa gtt cta caa agg att gaa              633
His Leu Tyr Arg Glu Leu Thr Cys Asp Glu Val Leu Gln Arg Ile Glu
            180                 185                 190 tct ttg gaa gaa gaa att atc tca aaa gga att aaa ctt gtg att ctt              681
Ser Leu Glu Glu Glu Ile Ile Ser Lys Gly Ile Lys Leu Val Ile Leu
195                 200                 205 gac tct gtt gct tct gtg gtc aga aag gag ttt gat gca caa ctt caa              729
Asp Ser Val Ala Ser Val Val Arg Lys Glu Phe Asp Ala Gln Leu Gln
210                 215                 220                 225 ggc aat ctc aaa gaa aga aac aag ttc ttg gca aga gag gca tcc tcc              777
Gly Asn Leu Lys Glu Arg Asn Lys Phe Leu Ala Arg Glu Ala Ser Ser
                230                 235                 240 ttg aag tat ttg gct gag gag ttt tca atc cca gtt atc ttg acg aat              825
Leu Lys Tyr Leu Ala Glu Glu Phe Ser Ile Pro Val Ile Leu Thr Asn
            245                 250                 255 cag att aca acc cat ctg agt gga gcc ctg gct tct cag gca gac ctg              873
Gln Ile Thr Thr His Leu Ser Gly Ala Leu Ala Ser Gln Ala Asp Leu
        260                 265                 270 gtg tct cca gct gat gat ttg tcc ctg tct gaa ggc act tct gga tcc              921
Val Ser Pro Ala Asp Asp Leu Ser Leu Ser Glu Gly Thr Ser Gly Ser
275                 280                 285 agc tgt gtg ata gcc gca cta gga aat acc tgg agt cac agt gtg aat              969
Ser Cys Val Ile Ala Ala Leu Gly Asn Thr Trp Ser His Ser Val Asn
290                 295                 300                 305 acc cgg ctg atc ctc cag tac ctt gat tca gag aga aga cag att ctt             1017
Thr Arg Leu Ile Leu Gln Tyr Leu Asp Ser Glu Arg Arg Gln Ile Leu
                310                 315                 320 att gcc aag tcc cct ctg gct ccc ttc acc tca ttt gtc tac acc atc             1065
Ile Ala Lys Ser Pro Leu Ala Pro Phe Thr Ser Phe Val Tyr Thr Ile
            325                 330                 335 aag gag gaa ggc ctg gtt ctt caa gcc tat gga aat tcc tag                     1107
Lys Glu Glu Gly Leu Val Leu Gln Ala Tyr Gly Asn Ser
        340                 345                 350 agacagataa atgtgcaaac ctgttcatct tgccaagaaa aatccgcttt tttgccacag           1167
aaacaaaata ttgggaaaga gtcttgtggt gaaacaccca tcgttctttg ctaaaacatt           1227
tggttgctac tgtgtagact cagcttaagt catggaattc tagaggatgt atctcacaag           1287
taggatcaag aacaagccca acagtaatct gcatcataag ctgatttgat accatggcac           1347
tgacaatggg cactgatttg ataccatggc actgacatgg gcacacaggg aacaggaaat           1407
gggaatgaga gcaagggttg ggttgtgttc gtggaacaca taggtttttt ttttttaact           1467
ttctctttct aaaatatttc attttgatgg aggtgaaatt tatataagat gaaattaacc           1527
attttaaagt aaacaattcc gtggcaacta gatatcatga tgtgcaacca gcatctctgt           1587
ctagttccaa atattttcat caccccaaaa gcaagaccca taaccattat gcaagtgttc           1647
ctatttcccc ctcctcccag ctcctggaaa cccaccaatc tactttgttg ctatggcttt           1707
acctattctg gatatttcat ataaatggaa tcatatagtg tcataaaaaa aaaaaaa              1764
```

<210> SEQ ID NO 2
<211> LENGTH: 350

```
<212> TYPE: PRT
<213> ORGANISM: Homo sapiens

<400> SEQUENCE: 2

Met Gly Ser Lys Lys Leu Lys Arg Val Gly Leu Ser Gln Glu Leu Cys
 1               5                  10                  15

Asp Arg Leu Ser Arg His Gln Ile Leu Thr Cys Gln Asp Phe Leu Cys
            20                  25                  30

Leu Ser Pro Leu Glu Leu Met Lys Val Thr Gly Leu Ser Tyr Arg Gly
        35                  40                  45

Val His Glu Leu Leu Cys Met Val Ser Arg Ala Cys Ala Pro Lys Met
    50                  55                  60

Gln Thr Ala Tyr Gly Ile Lys Ala Gln Arg Ser Ala Asp Phe Ser Pro
65                  70                  75                  80

Ala Phe Leu Ser Thr Thr Leu Ser Ala Leu Asp Glu Ala Leu His Gly
                85                  90                  95

Gly Val Ala Cys Gly Ser Leu Thr Glu Ile Thr Gly Pro Pro Gly Cys
            100                 105                 110

Gly Lys Thr Gln Phe Cys Ile Met Met Ser Ile Leu Ala Thr Leu Pro
        115                 120                 125

Thr Asn Met Gly Gly Leu Glu Gly Ala Val Val Tyr Ile Asp Thr Glu
130                 135                 140

Ser Ala Phe Ser Ala Glu Arg Leu Val Glu Ile Ala Glu Ser Arg Phe
145                 150                 155                 160

Pro Arg Tyr Phe Asn Thr Glu Glu Lys Leu Leu Leu Thr Ser Ser Lys
                165                 170                 175

Val His Leu Tyr Arg Glu Leu Thr Cys Asp Glu Val Leu Gln Arg Ile
            180                 185                 190

Glu Ser Leu Glu Glu Glu Ile Ile Ser Lys Gly Ile Lys Leu Val Ile
        195                 200                 205

Leu Asp Ser Val Ala Ser Val Val Arg Lys Glu Phe Asp Ala Gln Leu
210                 215                 220

Gln Gly Asn Leu Lys Glu Arg Asn Lys Phe Leu Ala Arg Glu Ala Ser
225                 230                 235                 240

Ser Leu Lys Tyr Leu Ala Glu Glu Phe Ser Ile Pro Val Ile Leu Thr
                245                 250                 255

Asn Gln Ile Thr Thr His Leu Ser Gly Ala Leu Ala Ser Gln Ala Asp
            260                 265                 270

Leu Val Ser Pro Ala Asp Asp Leu Ser Leu Ser Glu Gly Thr Ser Gly
        275                 280                 285

Ser Ser Cys Val Ile Ala Ala Leu Gly Asn Thr Trp Ser His Ser Val
290                 295                 300

Asn Thr Arg Leu Ile Leu Gln Tyr Leu Asp Ser Glu Arg Arg Gln Ile
305                 310                 315                 320

Leu Ile Ala Lys Ser Pro Leu Ala Pro Phe Thr Ser Phe Val Tyr Thr
                325                 330                 335

Ile Lys Glu Glu Gly Leu Val Leu Gln Ala Tyr Gly Asn Ser
            340                 345                 350

<210> SEQ ID NO 3
<211> LENGTH: 1295
<212> TYPE: DNA
<213> ORGANISM: Homo sapiens
<220> FEATURE:
<221> NAME/KEY: CDS
<222> LOCATION: (43)..(1173)
```

<400> SEQUENCE: 3

```
gtgcggagtt tggctgctcc ggggttagca ggtgagcctg cg atg cgc ggg aag                54
                                                 Met Arg Gly Lys
                                                  1 acg ttc cgc ttt gaa atg cag cgg gat ttg gtg agt ttc ccg ctg tct              102
Thr Phe Arg Phe Glu Met Gln Arg Asp Leu Val Ser Phe Pro Leu Ser
  5              10                 15                  20 cca gcg gtg cgg gtg aag ctg gtg tct gcg ggg ttc cag act gct gag              150
Pro Ala Val Arg Val Lys Leu Val Ser Ala Gly Phe Gln Thr Ala Glu
             25                  30                  35 gaa ctc cta gag gtg aaa ccc tcc gag ctt agc aaa gaa gtt ggg ata              198
Glu Leu Leu Glu Val Lys Pro Ser Glu Leu Ser Lys Glu Val Gly Ile
         40                  45                  50 tct aaa gca gaa gcc tta gaa act ctg caa att atc aga aga gaa tgt              246
Ser Lys Ala Glu Ala Leu Glu Thr Leu Gln Ile Ile Arg Arg Glu Cys
     55                  60                  65 ctc aca aat aaa cca aga tat gct ggt aca tct gag tca cac aag aag              294
Leu Thr Asn Lys Pro Arg Tyr Ala Gly Thr Ser Glu Ser His Lys Lys
 70                  75                  80 tgt aca gca ctg gaa ctt ctt gag cag gag cat acc cag ggc ttc ata              342
Cys Thr Ala Leu Glu Leu Leu Glu Gln Glu His Thr Gln Gly Phe Ile
 85                  90                  95                 100 atc acc ttc tgt tca gca cta gat gat att ctt ggg ggt gga gtg ccc              390
Ile Thr Phe Cys Ser Ala Leu Asp Asp Ile Leu Gly Gly Gly Val Pro
                105                 110                 115 tta atg aaa aca aca gaa att tgt ggt gca cca ggt gtt gga aaa aca              438
Leu Met Lys Thr Thr Glu Ile Cys Gly Ala Pro Gly Val Gly Lys Thr
                120                 125                 130 caa tta tgt atg cag ttg gca gta gat gtg cag ata cca gaa tgt ttt              486
Gln Leu Cys Met Gln Leu Ala Val Asp Val Gln Ile Pro Glu Cys Phe
            135                 140                 145 gga gga gtg gca ggt gaa gca gtt ttt att gat aca gag gga agt ttt              534
Gly Gly Val Ala Gly Glu Ala Val Phe Ile Asp Thr Glu Gly Ser Phe
150                 155                 160 atg gtt gat aga gtg gta gac ctt gct act gcc tgc att cag cac ctt              582
Met Val Asp Arg Val Val Asp Leu Ala Thr Ala Cys Ile Gln His Leu
165                 170                 175                 180 cag ctt ata gca gaa aaa cac aag gga gag gaa cac cga aaa gct ttg              630
Gln Leu Ile Ala Glu Lys His Lys Gly Glu Glu His Arg Lys Ala Leu
                185                 190                 195 gag gat ttc act ctt gat aat att ctt tct cat att tat tat ttt cgc              678
Glu Asp Phe Thr Leu Asp Asn Ile Leu Ser His Ile Tyr Tyr Phe Arg
            200                 205                 210 tgt cgt gac tac aca gag tta ctg gca caa gtt tat ctt ctt cca gat              726
Cys Arg Asp Tyr Thr Glu Leu Leu Ala Gln Val Tyr Leu Leu Pro Asp
        215                 220                 225 ttc ctt tca gaa cac tca aag gtt cga cta gtg ata gtg gat ggt att              774
Phe Leu Ser Glu His Ser Lys Val Arg Leu Val Ile Val Asp Gly Ile
    230                 235                 240 gct ttt cca ttt cgt cat gac cta gat gac ctg tct ctt cgt act cgg              822
Ala Phe Pro Phe Arg His Asp Leu Asp Asp Leu Ser Leu Arg Thr Arg
245                 250                 255                 260 tta tta aat ggc cta gcc cag caa atg atc agc ctt gca aat aat cac              870
Leu Leu Asn Gly Leu Ala Gln Gln Met Ile Ser Leu Ala Asn Asn His
                265                 270                 275 aga tta gct gta att tta acc aat cag atg aca aca aag att gat aga              918
Arg Leu Ala Val Ile Leu Thr Asn Gln Met Thr Thr Lys Ile Asp Arg
            280                 285                 290
```

```
aat cag gcc ttg ctt gtt cct gca tta ggg gaa agt tgg gga cat gct    966
Asn Gln Ala Leu Leu Val Pro Ala Leu Gly Glu Ser Trp Gly His Ala
            295                 300                 305 gct aca ata cgg cta atc ttt cat tgg gac cga aag caa agg ttg gca   1014
Ala Thr Ile Arg Leu Ile Phe His Trp Asp Arg Lys Gln Arg Leu Ala
        310                 315                 320 aca ttg tac aag tca ccc agc cag aag gaa tgc aca gta ctg ttt caa   1062
Thr Leu Tyr Lys Ser Pro Ser Gln Lys Glu Cys Thr Val Leu Phe Gln
325                 330                 335                 340 atc aaa cct cag gga ttt aga gat act gtt gtt act tct gca tgt tca   1110
Ile Lys Pro Gln Gly Phe Arg Asp Thr Val Val Thr Ser Ala Cys Ser
                345                 350                 355 ttg caa aca gaa ggt tcc ttg agc acc cgg aaa cgg tca cga gac cca   1158
Leu Gln Thr Glu Gly Ser Leu Ser Thr Arg Lys Arg Ser Arg Asp Pro
            360                 365                 370 gag gaa gaa tta taa cccagaaaca aatctcaaag tgtacaaatt tattgatgtt   1213
Glu Glu Glu Leu
            375 gtgaaatcaa tgtgtacaag tggacttgtt accttaaagt ataaataaac acactatggc  1273 atgaatgaaa aaaaaaaaaa aa                                          1295

<210> SEQ ID NO 4
<211> LENGTH: 376
<212> TYPE: PRT
<213> ORGANISM: Homo sapiens

<400> SEQUENCE: 4

Met Arg Gly Lys Thr Phe Arg Phe Glu Met Gln Arg Asp Leu Val Ser
 1               5                  10                  15

Phe Pro Leu Ser Pro Ala Val Arg Val Lys Leu Val Ser Ala Gly Phe
            20                  25                  30

Gln Thr Ala Glu Glu Leu Leu Glu Val Lys Pro Ser Glu Leu Ser Lys
        35                  40                  45

Glu Val Gly Ile Ser Lys Ala Glu Ala Leu Glu Thr Leu Gln Ile Ile
    50                  55                  60

Arg Arg Glu Cys Leu Thr Asn Lys Pro Arg Tyr Ala Gly Thr Ser Glu
65                  70                  75                  80

Ser His Lys Lys Cys Thr Ala Leu Glu Leu Leu Glu Gln Glu His Thr
                85                  90                  95

Gln Gly Phe Ile Ile Thr Phe Cys Ser Ala Leu Asp Asp Ile Leu Gly
            100                 105                 110

Gly Gly Val Pro Leu Met Lys Thr Thr Glu Ile Cys Gly Ala Pro Gly
        115                 120                 125

Val Gly Lys Thr Gln Leu Cys Met Gln Leu Ala Val Asp Val Gln Ile
    130                 135                 140

Pro Glu Cys Phe Gly Gly Val Ala Gly Glu Ala Val Phe Ile Asp Thr
145                 150                 155                 160

Glu Gly Ser Phe Met Val Asp Arg Val Val Asp Leu Ala Thr Ala Cys
                165                 170                 175

Ile Gln His Leu Gln Leu Ile Ala Glu Lys His Lys Gly Glu Glu His
            180                 185                 190

Arg Lys Ala Leu Glu Asp Phe Thr Leu Asp Asn Ile Leu Ser His Ile
        195                 200                 205

Tyr Tyr Phe Arg Cys Arg Asp Tyr Thr Glu Leu Leu Ala Gln Val Tyr
    210                 215                 220

Leu Leu Pro Asp Phe Leu Ser Glu His Ser Lys Val Arg Leu Val Ile
```

-continued

```
                    225                 230                 235                 240
            Val Asp Gly Ile Ala Phe Pro Phe Arg His Asp Leu Asp Leu Ser
                            245                 250                 255
            Leu Arg Thr Arg Leu Leu Asn Gly Leu Ala Gln Gln Met Ile Ser Leu
                        260                 265                 270
            Ala Asn Asn His Arg Leu Ala Val Ile Leu Thr Asn Gln Met Thr Thr
                        275                 280                 285
            Lys Ile Asp Arg Asn Gln Ala Leu Leu Val Pro Ala Leu Gly Glu Ser
                        290                 295                 300
            Trp Gly His Ala Ala Thr Ile Arg Leu Ile Phe His Trp Asp Arg Lys
            305                 310                 315                 320
            Gln Arg Leu Ala Thr Leu Tyr Lys Ser Pro Ser Gln Lys Glu Cys Thr
                        325                 330                 335
            Val Leu Phe Gln Ile Lys Pro Gln Gly Phe Arg Asp Thr Val Val Thr
                        340                 345                 350
            Ser Ala Cys Ser Leu Gln Thr Glu Gly Ser Leu Ser Thr Arg Lys Arg
                        355                 360                 365
            Ser Arg Asp Pro Glu Glu Glu Leu
                370                 375

<210> SEQ ID NO 5
<211> LENGTH: 1598
<212> TYPE: DNA
<213> ORGANISM: Homo sapiens
<220> FEATURE:
<221> NAME/KEY: CDS
<222> LOCATION: (125)..(994)
<220> FEATURE:
<221> NAME/KEY: misc_feature
<222> LOCATION: (270)..(270)
<223> OTHER INFORMATION: n is any nucleotide residues
<220> FEATURE:
<221> NAME/KEY: misc_feature
<222> LOCATION: (271)..(271)
<223> OTHER INFORMATION: n is any nucleotide residues

<400> SEQUENCE: 5
attcggcacg agcgcgcctg tgtcctctct aggaaggggt aggggagggg cgtctggaga        60 ggacccccg cgaatgccca cgtgacgtgc agtcccctg gggctgttcc ggcctgcggg        120 gaac atg ggc gtg ctc agg gtc gga ctg tgc cct ggc ctt acc gag gag        169
     Met Gly Val Leu Arg Val Gly Leu Cys Pro Gly Leu Thr Glu Glu
      1               5                  10                  15 atg atc cag ctt ctc agg agc cac agg atc aag aca gtg gtg gac ctg        217
Met Ile Gln Leu Leu Arg Ser His Arg Ile Lys Thr Val Val Asp Leu
             20                  25                  30 gtt tct gca gac ctg gaa gag gta gct cag aaa tgt ggc ttg tct tac        265
Val Ser Ala Asp Leu Glu Glu Val Ala Gln Lys Cys Gly Leu Ser Tyr
         35                  40                  45 aag tnn ctt gat aaa ctg ctt gat gct ggt ctc tat act gga gaa gtg        313
Lys Xaa Leu Asp Lys Leu Leu Asp Ala Gly Leu Tyr Thr Gly Glu Val
         50                  55                  60 act gaa att gta gga ggc cca ggt agc ggc aaa act cag gta tgt ctc        361
Thr Glu Ile Val Gly Gly Pro Gly Ser Gly Lys Thr Gln Val Cys Leu
     65                  70                  75 tgt atg gca gca aat gtg gcc cat ggc ctg cag caa aac gtc cta tat        409
Cys Met Ala Ala Asn Val Ala His Gly Leu Gln Gln Asn Val Leu Tyr
 80                  85                  90                  95 gta gat tcc aat gga ggg ctg aca gct tcc cgc ctc ctc cag ctg ctt        457
Val Asp Ser Asn Gly Gly Leu Thr Ala Ser Arg Leu Leu Gln Leu Leu
                100                 105                 110
```

```
cag gct aaa acc cag gat gag gag gaa cag gca gaa gct ctc cgg agg      505
Gln Ala Lys Thr Gln Asp Glu Glu Glu Gln Ala Glu Ala Leu Arg Arg
            115                 120                 125 atc cag gtg gtg cat gca ttt gac atc ttc cag atg ctg gat gtg ctg      553
Ile Gln Val Val His Ala Phe Asp Ile Phe Gln Met Leu Asp Val Leu
            130                 135                 140 cag gag ctc cga ggc act gtg gcc cag cag gtg act ggt tct tca gga      601
Gln Glu Leu Arg Gly Thr Val Ala Gln Gln Val Thr Gly Ser Ser Gly
145                 150                 155 act gtg aag gtg gtg gtt gtg gac tcg gtc act gcg gtg gtt tcc cca      649
Thr Val Lys Val Val Val Val Asp Ser Val Thr Ala Val Val Ser Pro
160                 165                 170                 175 ctt ctg gga ggt cag cag agg gaa ggc ttg gcc ttg atg atg cag ctg      697
Leu Leu Gly Gly Gln Gln Arg Glu Gly Leu Ala Leu Met Met Gln Leu
            180                 185                 190 gcc cga gag ctg aag acc ctg gcc cgg gac ctt ggc atg gca gtg gtg      745
Ala Arg Glu Leu Lys Thr Leu Ala Arg Asp Leu Gly Met Ala Val Val
            195                 200                 205 gtg acc aac cac ata act cga gac agg gac agc ggg agg ctc aaa cct      793
Val Thr Asn His Ile Thr Arg Asp Arg Asp Ser Gly Arg Leu Lys Pro
            210                 215                 220 gcc ctc gga cgc tcc tgg agc ttt gtg ccc agc act cgg att ctc ctg      841
Ala Leu Gly Arg Ser Trp Ser Phe Val Pro Ser Thr Arg Ile Leu Leu
225                 230                 235 gac acc atc gag gga gca gga gca tca ggc ggc cgg cgc atg gcg tgt      889
Asp Thr Ile Glu Gly Ala Gly Ala Ser Gly Gly Arg Arg Met Ala Cys
240                 245                 250                 255 ctg gcc aaa tct tcc cga cag cca aca ggt ttc cag gag atg gta gac      937
Leu Ala Lys Ser Ser Arg Gln Pro Thr Gly Phe Gln Glu Met Val Asp
            260                 265                 270 att ggg acc tgg ggg acc tca gag cag agt gcc aca tta cag ggt gat      985
Ile Gly Thr Trp Gly Thr Ser Glu Gln Ser Ala Thr Leu Gln Gly Asp
            275                 280                 285 cag aca tga cctgtgctgt tgtttgggaa acagggaagc attgggacc              1034
Gln Thr
    290 cctcccaact tttcttccca gtaacgcctg ctgtttactg ccacctggca ctggtgacta   1094 cagacgttct caggctggcc agaagagaca tcttgggttc cttggcctca ctctctgtaa   1154 gcatataaac cacaggcgaa agaggatgct gcattgcgag gacccagaaa ttcatactgg   1214 tgccacgttt ccttcccta tttctaacgt gtatgtttct ggtggaaacc aagttcaccc    1274 tggctgggag catctctgat gaggcatgct ggcgactgga tggataatcc tgtgcatcac   1334 cattgtgtcc tgtgctccct cctagcgcag tggccaagcc gggaaagcct ctaacttgcc   1394 tttgctgctg ctgcctttt tttcttttgt ctctgccttt ccatttgtta gatggggggcc   1454 cactcttcct tagctctgtc tctgagttac tgggtggaaa taagcttata aatgaaatac   1514 tcttcttcat ctctgttttg ctcttaaaaa tataaaagg caattccccg aaaaaaaaaa    1574 aaaaaaaaaa aaaaaaaaaa aaaa                                          1598

<210> SEQ ID NO 6
<211> LENGTH: 289
<212> TYPE: PRT
<213> ORGANISM: Homo sapiens
<220> FEATURE:
<221> NAME/KEY: misc_feature
<222> LOCATION: (49)..(49)
<223> OTHER INFORMATION: Xaa is any amino acid residues
```

-continued

```
<400> SEQUENCE: 6

Met Gly Val Leu Arg Val Gly Leu Cys Pro Gly Leu Thr Glu Glu Met
 1               5                  10                  15

Ile Gln Leu Leu Arg Ser His Arg Ile Lys Thr Val Val Asp Leu Val
             20                  25                  30

Ser Ala Asp Leu Glu Glu Val Ala Gln Lys Cys Gly Leu Ser Tyr Lys
             35                  40                  45

Xaa Leu Asp Lys Leu Leu Asp Ala Gly Leu Tyr Thr Gly Glu Val Thr
         50                  55                  60

Glu Ile Val Gly Gly Pro Gly Ser Gly Lys Thr Gln Val Cys Leu Cys
 65                  70                  75                  80

Met Ala Ala Asn Val Ala His Gly Leu Gln Gln Asn Val Leu Tyr Val
                 85                  90                  95

Asp Ser Asn Gly Gly Leu Thr Ala Ser Arg Leu Leu Gln Leu Leu Gln
                100                 105                 110

Ala Lys Thr Gln Asp Glu Glu Gln Ala Glu Ala Leu Arg Arg Ile
            115                 120                 125

Gln Val Val His Ala Phe Asp Ile Phe Gln Met Leu Asp Val Leu Gln
    130                 135                 140

Glu Leu Arg Gly Thr Val Ala Gln Gln Val Thr Gly Ser Ser Gly Thr
145                 150                 155                 160

Val Lys Val Val Val Asp Ser Val Thr Ala Val Val Ser Pro Leu
                165                 170                 175

Leu Gly Gly Gln Gln Arg Glu Gly Leu Ala Leu Met Met Gln Leu Ala
            180                 185                 190

Arg Glu Leu Lys Thr Leu Ala Arg Asp Leu Gly Met Ala Val Val Val
    195                 200                 205

Thr Asn His Ile Thr Arg Asp Arg Asp Ser Gly Arg Leu Lys Pro Ala
210                 215                 220

Leu Gly Arg Ser Trp Ser Phe Val Pro Ser Thr Arg Ile Leu Leu Asp
225                 230                 235                 240

Thr Ile Glu Gly Ala Gly Ala Ser Gly Gly Arg Arg Met Ala Cys Leu
                245                 250                 255

Ala Lys Ser Ser Arg Gln Pro Thr Gly Phe Gln Glu Met Val Asp Ile
            260                 265                 270

Gly Thr Trp Gly Thr Ser Glu Gln Ser Ala Thr Leu Gln Gly Asp Gln
        275                 280                 285

Thr
```

TARGET OF ANTICANCER AGENT

This application is the national phase under 35 U.S.C. § 371 of PCT International Application No. PCT/JP00/04739 which has an International filing date of Jul. 14, 2000, which designated the United States of America.

TECHNICAL FIELD

The present invention relates to a target for an anticancer agent and a technique using the same, which are useful for the treatment of cancer.

BACKGROUND ART

Double-strand DNA breakages occur frequently during DNA repair and are produced by ionizing radiation and certain chemicals [Haber, J. E., *Trends Biochem. Sci.,* 24, 271–275 (1999)]. A single unrepaired double-strand DNA breakage is believed to cause cell death in yeast and vertebrate cells [Bennett, C. B. et al., *Proc. Natl. Acad. Sci. USA,* 90, 5613–5617; Huang, L. C. et al., *Proc. Natl. Acad. Sci. USA,* 93, 4827–4832 (1996)].

In yeast, homologous recombination repair is a major DNA breakage repair pathway. The above-mentioned homologous recombination repair pathway has been conserved from yeast to human [Shinohara, A. et al., *Nat. Genet.,* 4, 239–243 (1993); Siede, W. et al., *Genetics,* 142, 91–102 (1996); Boulton, S. J. et al., *Nucleic Acids Res.,* 24, 4639–4648 (1996a); Boulton, S. J. et al., *EMBO J.,* 15, 5093–5103 (1996b); Bezzubova, O. Y. et al., *Cell,* 89, 185–193 (1997); Essers, J. et al., *Cell,* 89, 195–204 (1997); Thompson, L. H. et al., *Biochimie,* 81, 87–105 (1999)].

Presently, the analysis of radiosensitive yeast mutants has revealed numbers of key genes involved in the homologous recombination repair. The genes include, for instance, the Rad52 epistasis group and the like [Shinohara, A. et al., *Trends Biochem. Sci.,* 20, 387–391 (1995); Baumann, P. et al., *Trends Biochem. Sci.,* 23, 247–251; Kanaar, R. et al., *Trends Cell Biol.,* 8, 483–489 (1998)].

Among the members of the RAD52 epistasis group, the structure and function of Rad51 have been conserved to a remarkable degree among all eukaryotes. The above-mentioned Rad51 structurally and functionally resembles *Escherichia coli* recombination protein RecA [reviewed in Kowalczykowski, S. C. et al., *Experientia,* 50, 204–15 (1994)]. Lethality of Rad51-deficient cells [Tsuzuki. T et al., *Proc. Natl. Acad. Sci. USA,* 93, 6236–6240 (1996); Lim, D. S. et al., *Mol. Cell Biol.,* 16, 7133–7143 (1996); Sonoda. E. et al., *EMBO. J.,* 17, 598–608 (1998)] has suggested that Rad51 plays a central role in the homologous recombination repair in vertebrate cells [Bezzubova, O. Y. et al., *Cell,* 89, 185–193 (1997); the above-mentioned Essers et al. (1997); Rijkers, T. et al., *Mol. Cell Biol.,* 18, 6423–6429 (1998); Yamaguchi-Iwai, Y. et al., *Mol. Cell. Biol.,* 18, 6430–6435 (1998)].

However, many of the detailed functions and roles for other Rad52 epistasis groups are yet unrevealed at the current situation.

DISCLOSURE OF INVENTION

An object of the present invention is to provide a target molecule (a nucleic acid, a peptide) which is useful for developing an anticancer agent having an action for enhancing the sensitivity of a cell to a DNA-damaging factor. Also, an object of the present invention is to provide a screening method for an anticancer agent having a DNA-damaging action, and a cell which is suitable for the screening method. Further, an object of the present invention is to provide a screening method for a controlling agent for DNA repair, which can be applied to an anticancer agent, a prophylactic agent for cancer, or the like.

Concretely, the present invention relates to:

[1] a mutant Rad51 paralog gene having substitution, deletion, insertion or addition of at least one base in:

(A) a nucleotide sequence selected from the group consisting of SEQ ID NOs 1, 3 and 5; or (B) a nucleotide sequence different from the nucleic acid of the (A) above via degeneracy, wherein a protein encoded thereby shows an activity for enhancing sensitivity of a cell to a DNA-damaging factor;

[2] a mutant Rad51 paralog peptide having substitution, deletion, insertion or addition of at least one amino acid residue in an amino acid sequence selected from the group consisting of SEQ ID NOs: 2, 4 and 6, wherein the mutant Rad51 paralog peptide shows an activity for enhancing sensitivity of a cell to a DNA-damaging factor;

[3] a transformed cell having the gene of the [1] above;

[4] a screening method for a drug having a DNA-damaging action, comprising the steps of:

(1) contacting a test substance with the transformed cell of the [3] above; and (2) evaluating a response of the cell obtained in step (1); and

[5] a screening method for a controlling agent for DNA repair, comprising the steps of:

(I) contacting a test substance with a transformed cell having a nucleic acid comprising (A) a nucleotide sequence selected from the group consisting of SEQ ID NOs 1, 3 and 5; or (B) a nucleotide sequence different from the nucleic acid of the (A) above via degeneracy; and (II) evaluating a homologous recombination repair capacity in the cell.

BEST MODE FOR CARRYING OUT THE INVENTION

Figure 1:
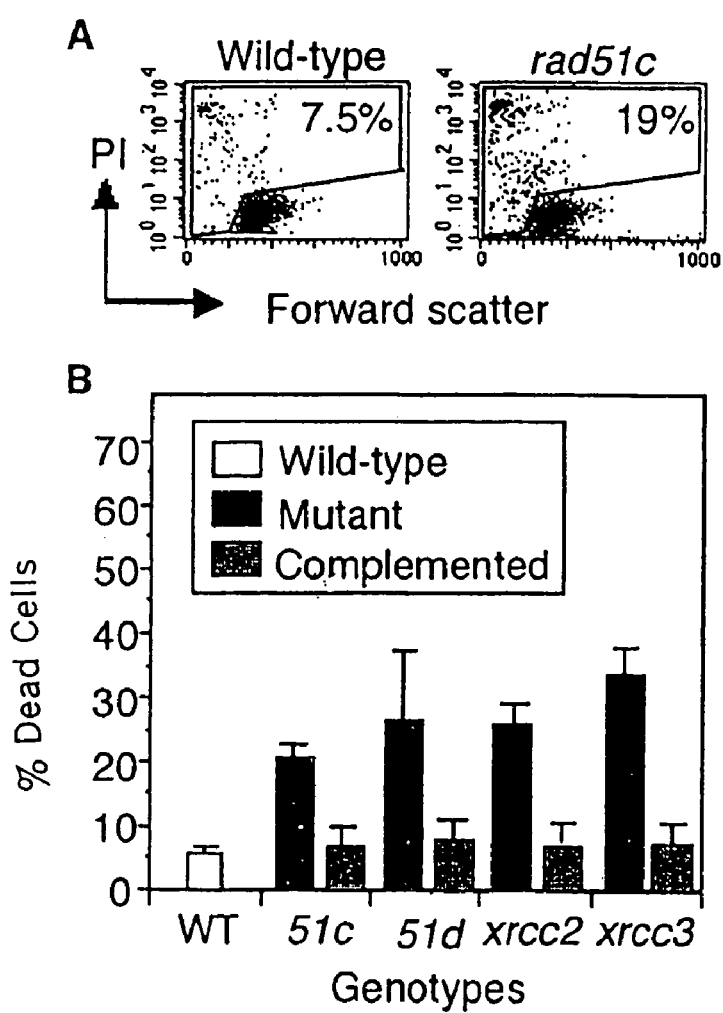
FIG. 1 is a diagram showing the results for evaluating lowered viability in mutant cultures. The panel (A) shows the results in which the level of spontaneous cell death was evaluated by flow cytometric analysis using propidium iodide (PI) uptake (Y axis) and forward scatter showing a cell size (X axis). Numbers show the percentage of dead (PI-bright and PI-dim/small) cells, and the solid line separates live cells from dead cells. In the panel (B), bars represent the level of spontaneous cell death in indicated genotypes.

The present invention is based on a surprising finding by the present inventors that a Rad51 paralog peptide, concretely a cell deficient in each of Rad51B, Rad51C and Rad51D genes, shows high sensitivity to a DNA-damaging factor, concretely cisplatin, mitomycin C or the like.

In view of the above finding, there are provided an application to screening of a drug having a higher anticancer action when the DNA damaging factor, for instance, cisplatin, mitomycin C or the like is used as an anticancer agent, and an application to screening of a drug capable of controlling an action of Rad51 paralog peptide.

Also, the present invention is based on an excellent technical idea that the proliferating cells such as cancer are led to death by suppression of the homologous recombination.

In the present specification, the term "paralog" is used to refer to a group of plural genes having high structural resemblance with each other in a single species, wherein the genes are generated by a duplication of single ancestor gene, or protein products thereof.

The results in Examples set forth below and other studies [Johnson, R. D. et al., *Nature*, 401, 397–399 (1999); Pierce, A. J. et al., *Genes Dev.*, 13, 2633–2638 (1999) and the like] show that all five kinds of the Rad51 paralogs are important for homologous recombination repair in vertebrate cells. Remarkably, mutant clones for each Rad51 paralog are phenotypically similar, suggesting that each protein is vitally involved in a particular process in homologous recombination repair. On the other hand, two hybrid analyses suggest that each Rad51 paralog appears to have different interacting partners within the family and together can form a single complex [reviewed in Dosanjh, M. K. et al., *Nucleic Acids Res.*, 26, 1179–1184 (1998); Liu, N. et al., *Mol. Cell*, 1, 783–793 (1998); the above-mentioned Thompson et al., (1999)]. These biochemical results combined with the genetic data by the present inventors are consistent with the action of the Rad51 paralogs as a single functional unit during homologous recombination repair.

The data given in Examples set forth below have suggested that yeast Rad51 paralogs, Rad55 and Rad57 are involved in the formation of nucleoprotein filaments involving Rad51. First, protein interactions between Rad51 and Rad55 and those between Rad55 and Rad57 suggest that these molecules act in multiprotein complexes. Second, the repair defects of rad55/57 mutants are partially suppressed by the overexpression of Rad51 [Hays, S. L. et al., *Proc. Natl. Acad. Sci. USA*, 92, 6925–6929 (1995); Johnson, R. D. et al., *Mol. Cell Biol.*, 15, 4843–4850 (1995)]. Third, biochemical analysis points out the Rad55/57 heterodimer acting as a cofactor for promoting an assembly of Rad51-ssDNA nucleoprotein filaments in the presence of RPA [Sung, P., *Genes Dev.*, 11, 1111–1121 (1997)]. These results support the idea that Rad55 and Rad57 are involved in homologous recombination repair by forming a complex which interacts with Rad51 to promote the formation of Rad51 nucleoprotein filaments.

The functional interactions between Rad51 and Rad51 paralogs have been investigated in the genetic system of the present invention. The overexpression of human Rad51 at least partially normalized the deficiency of each Rad51-paralog mutant in repairing genomic damage by γ-rays, cisplatin, and MMC. This observation implies that each Rad51 paralog participates in homologous recombination repair by facilitating the function of Rad51, as does Rad55/Rad57 in yeast. In addition, defective Rad51 focus formation in Rad51-paralog-mutants suggests that the Rad51 paralogs can promote the assembly of Rad51 at DNA lesions. A similar situation applies to yeast, in which case mutations in Rad55 and Rad57 prevent the appearance of Rad51 foci during meiosis [Gaisor, S. L. et al., *Genes Dev.*, 12, 2208–2221 (1998)]. These observational results show that the Rad51 paralogs facilitate the function of Rad51 by promoting the assembly of Rad51 in nucleoprotein filaments.

While the data in Examples set forth below suggest that the Rad51 paralogs can be involved in homologous recombination by association with Rad51, Kurumizaka et al. (in preparation for contribution of an article) recently found that a complex composed of Rad51C and XRCC3 shows a strong homologous pairing activity, but not showing a branch migration activity, in the absence of Rad51 in vitro. This in vitro activity might promote intragenic double-stranded DNA breakage-mediated homologous recombination repair in vivo, the level of which was reduced by 25- to 100-fold in mammalian XRCC2- and XRCC3-deficient cells and was not restored by transient transfection with human Rad51 [the above-mentioned Johnson et al. (1999); the above-mentioned Pierce et al. (1999)]. This drastic reduction in intragenic homologous recombination repair efficiencies was in marked contrast with only a few fold reduction in radiation resistance to γ-rays in late-S-phase [Cheong, N. et al., *Mutat. Res.*, 314, 77–85 (1994)]. In this case, induced double-stranded DNA breakages on one chromatid should be repaired by homologous recombination with the other intact sister chromatid [Takata, M. et al., *EMBO J.*, 17, 5497–5508 (1998)]. These observational results show the possibilities that some Rad51 paralogs are involved in an intragenic homologous recombination subpathway that does not require Rad51. Given that the Rad51 paralogs, but not Rad51, are expressed in some nondividing cells (e.g. all Rad51 paralogs are expressed in the brain), the Rad51 paralogs are possible to play a role in intragenic homologous recombination repair in resting cells of vertebrates.

According to Examples set forth below, it is shown that DNA damage induces Rad51 foci in a Rad51 paralog-dependent manner, and that all Rad51-paralog mutants are highly sensitive to cisplatin. Thus, each Rad51 paralog plays an important role in the response to this clinically important drug. Since XRCC2-deficient cells are shown to exhibit a drastic increase in chromosomal breakages following exposure to MMC [Tucker, J. D. et al., *Mutat. Res.*, 254, 143–152 (1991)], the formation of unrepaired double-stranded DNA breakages during abortive cross-link repair most likely explains the extremely high sensitivity of XRCC2-deficient cells to MMC.

The occurrence of homologous recombination repair during the normal meiotic cell cycle is suggested by the appearance of Rad51 foci in S phase and by spontaneous sister chromatid exchange. The sister chromatid exchanges are at least partially mediated by homologous recombination repair and occur at a frequency of about 3 exchanges per single cell cycle in a mammalian cell [Sonoda. et al., *Mol. Cell. Biol.*, 19, 5166–5169 (1999)]. In addition, the presence of excessive chromosome breakages in rad51 avian-cell mutant and mre11 avian-cell mutant indicates that homologous recombination repair plays an essential role in repairing potentially lethal chromosomal breakages that are likely to occur during DNA replication [Sonoda et al. (1998); Yamaguchi-Iwai et al., *EMBO J.*, 18, 6619–6629 (1999)]. Thus, defective homologous recombination repair exhibits a phenotype similar to that of the human chromosome instability syndromes, such as Bloom syndrome, Fanconi anemia and ataxia telangiectasia. These all show an increased incidence of cancer [reviewed in Meyn, M. S., *Curr. Top. Microbiol. Immunol.*, 221, 71–148 (1997)]. Given that Rad51 paralogs also function as tumor suppressor genes by maintaining the integrity of chromosomes, it is desirable to screen for mutations in these loci in various tumors. Indeed, chromosome translocation breakpoints within Rad51B at position 14q23–24 have been recently found in uterine leiomyomas [Schoenmakers, E. F. et al., *Cancer Res.*, 59, 19–23 (1999)].

The Brca2 cancer susceptibility protein is associated with Rad51 in mitotic cells and meiotic cells [Chen, J. et al., *Mol. Cell*, 2, 317–328 (1998a); Chen, J. et al., *Proc. Natl. Acad. Sci., USA*, 95, 5287–5292 (1998b)], suggesting a direct role of Brca2 in the homologous recombination repair. It is noteworthy that human Brca2-truncated mutant cells and murine Brca2-truncated mutant cells exhibit phenotypes: elevated spontaneous chromosomal aberrations [Patel, K. J. et al., *Mol. Cell*, 1, 347–357 (1998)], sensitivity to MMC [the above-mentioned Patel et al. (1998)], and defective Rad51 focus formation [Yuan, S. S. et al., *Cancer Res.*, 59, 3547–3551 (1999)], which are remarkably similar to the Rad51-paralog mutants. Thus, Brca2 is possible to participate in the formation of a complex involving the Rad51 paralogs, and acts as a cofactor of Rad51 during the homologous recombination repair. In addition to the presence of Brca2 homologs in vertebrates but not in yeast, the presence of five kinds of Rad51 paralogs in vertebrates instead of only two kinds in yeast (Rad55 and Rad57) shows that the assembly of Rad51 during homologous recombination repair is regulated in a more complicated manner in vertebrate cells. Indeed, although homologous recombination repair occurs efficiently in the G1 phase in diploid yeast [Kadyk, L. C. et al., *Genetics*, 132, 387–402 (1992)], there was no induction of Rad51 focus formation by ionizing radiation in the G1 phase in CHO hamster cells [Bishop, D. K. et al., *J. Biol. Chem.*, 273, 21482–21488 (1998)]. This finding shows that the assembly of Rad51 is possible to be actively suppressed in the G1 phase to prevent gene conversion between homologous chromosomes, which would result in loss of heterozygosity.

The above-mentioned Rad51 paralog peptide (hereinafter simply referred to "Rad51 paralog" in some cases) includes, for instance, Rad55 and Rad57 from *Saccharomyces cerevisiae*; and XRCC2 [Cartwright, R. et al., *Nucleic Acids Res.*, 26, 3084–3089 (1998); Liu, N. et al., *Mol. Cell*, 1, 783–793 (1998)], XRCC3 [Tebbs, R. S. et al., *Proc. Natl. Acad. Sci. USA*, 92, 6354–6358 (1995); the above-mentioned Liu et al. (1998)], Rad51B [Albala, J. S. et al., *Genomics*, 46, 476–479 (1997); Rice, M. C. et al., *Proc. Natl. Acad. Sci. USA*, 94, 7417–7422 (1997); Cartwright, R. et al., *Nucleic Acids Res.*, 26, 1653–1659 (1998)], Rad51C [the above-mentioned Dosanjh, M. K. et al. (1998)], and Rad51D [Pittman, D. L. et al., *Genomics*, 49, 103–111 (1998); Cartwright et al., *Nucleic Acids Res.*, 26, 1653–1659 (1998); Kawabata, M. et al., *Biochem. Biophys. Res. Commun.*, 1398, 353–358 (1998)], which are derived from vertebrates.

Among them, the vertebrate-derived, especially the five kinds of human-derived Rad51 paralogs (XRCC2, XRCC3, Rad51B, Rad51C and Rad51D) have only 20–30% identity with human Rad51 and show only less than 30% homology to each other. Also, the above-mentioned five kinds of human Rad51 paralogs show only less than 30% homology to yeast Rad55 and Rad57 [reviewed in Thacker, *Trends Genet.*, 15, 166–168 (1999)].

Unlike Rad51, none of the above-mentioned Rad51 paralog appears to interact with itself as in the case of yeast Rad55 and Rad57 [the above-mentioned Thompson et al. (1999)]. It is suggested that overexpression of Rad51 partially suppresses the DNA repair defect in rad55 and rad57 mutant yeast strains, whereby the Rad55 and Rad57 functionally cooperate with Rad51. This idea is supported by physical interactions between Rad51 and Rad55 and physical interactions between Rad55 and Rad57 [the above-mentioned Hays, S. L. et al. (1995); the above-mentioned Johnson, R. D. et al. (1995); Sung, P. (1997)]. Similarly, physical interactions occur between human Rad51 and XRCC3, between XRCC3 and Rad51C, between Rad51B and Rad51C, and between Rad51C and Rad51D [reviewed in the above-mentioned Thompson et al. (1999)]. These observation results show that Rad51 paralogs form a functional complex and cooperate with Rad51, in the same manner as in the yeast Rad55 and Rad57 proteins.

1. Mutant Rad51 Paralog Gene of the Present Invention

According to the present invention, there is provided a mutant Rad51 paralog gene, wherein a protein encoded thereby shows an activity for enhancing sensitivity of a cell to a DNA-damaging factor.

The mutant Rad51 paralog gene of the present invention includes a gene having substitution, deletion, insertion or addition of at least one base in:

(A) a nucleotide sequence selected from the group consisting of SEQ ID NOs: 1, 3 and 5; or (B) a nucleotide sequence different from the nucleic acid of the (A) above via degeneracy, wherein a protein encoded thereby shows an activity for enhancing sensitivity of a cell to a DNA-damaging factor.

The mutant Rad51 paralog gene of the present invention is one in which its encoded protein shows an activity for enhancing sensitivity of a cell to a DNA-damaging factor, especially has lowered or diminished homologous recombination repair capability. Therefore, when a DNA-damaging factor, for instance, cisplatin, mitomycin C or the like is used as an anticancer agent, the paralog gene is especially useful in the application for screening of a drug having a higher anticancer action.

Here, the above-mentioned nucleotide sequences of SEQ ID NOs: 1, 3 and 5 are sequences of a gene encoding Rad51B, a gene encoding Rad51C and a gene encoding Rad51D. Incidentally, genes encoding Rad51B, Rad51C and Rad51D may be referred to rad51b, rad51c and rad51d, respectively, in some cases.

The above-mentioned protein includes a mutant peptide which is deficient of the function of Rad51B, Rad51C and Rad51D.

More concretely, the above-mentioned mutant Rad51 paralog gene includes:

(a) a nucleotide sequence in which a region of 463rd to 573rd bases is deleted or substituted with a sequence of a marker gene in the nucleotide sequence of SEQ ID NO: 1, (b) a nucleotide sequence in which a region of 628th to 747th bases is deleted or substituted with a sequence of a marker gene in the nucleotide sequence of SEQ ID NO: 3, and (c) a nucleotide sequence in which a region of 536th to 583rd bases is deleted or substituted with a sequence of a marker gene in the nucleotide sequence of SEQ ID NO: 5, wherein a protein encoded thereby shows an activity for enhancing sensitivity of a cell to a DNA-damaging factor.

In the present invention, the mutant Rad51 paralog gene is not limited to the gene having any of the sequences of the (a) to (c) above. For instance, there is included a gene having a nucleotide sequence having substitution, deletion, insertion or addition of at least one base in any of SEQ ID NOs: 1, 3 and 5 so that the encoded protein is deficient of homologous recombination repair capacity, wherein a protein encoded thereby shows an activity for enhancing sensitivity of a cell to a DNA-damaging factor.

Here, substitution, deletion, insertion or addition can be easily obtained by one of ordinary skill in the art by such a method as conventional site-directed mutagenesis method or PCR method. The techniques are described in textbooks, for instance, *Molecular Cloning: A Laboratory Manual*, 2nd Ed. [*Molecular Cloning: A Laboratory Manual*, 2nd Ed., Cold Spring Harbor Laboratory Press (1989)], and the like. The number of substitution, deletion, insertion or addition can be properly selected within the range in which the protein encoded by the resulting gene shows an activity for enhancing sensitivity of a cell to a DNA-damaging factor.

The above-mentioned mutant Rad51 paralog gene can be obtained by:

1) introducing a desired mutation (substitution, deletion, insertion and addition) into the nucleotide sequence of SEQ ID NOs: 1, 3 and 5 mentioned above to give a mutant gene, and 2) evaluating an expression product of the resulting mutant gene for an activity for enhancing sensitivity of a cell to a DNA-damaging factor, optionally homologous recombination repair capacity.

Here, the phrase "activity for enhancing sensitivity of a cell to a DNA-damaging factor" can be evaluated as described, for instance, in Example 3. Also, the term "homologous recombination repair capacity" can be evaluated by analyses such as the analysis for chromosomal aberrations, the analysis for sister chromatid exchanges, the analysis of targeted integration frequencies and the like as described in Example 2.

In the present invention, the DNA-damaging factor includes irradiation rays (γ-rays and the like), mitomycin C and cisplatin. Among them, mitomycin C and cisplatin possess a characteristic of forming a cross-link between the double strand of the DNA molecule, thereby specifically inhibiting only the DNA biosynthesis selectively, so that these substances can be used as an anticancer agent. The mutant Rad51 paralog gene of the present invention via the expression exhibits excellent effects such that the sensitivity of a cell to an anticancer agent comprising the DNA-damaging factor as mentioned above can be improved.

The above-mentioned marker gene may be any of those which are deficient of the function of the Rad51 paralog gene and can facilitate selection of the desired mutant Rad51 paralog gene, and includes drug resistance genes, for instance, puromycin resistance gene, neomycin resistance gene, histidinol resistance gene, Ecogpt gene, blastocitidin resistance gene, hygromycin resistance gene, and the like.

The mutant Rad51 paralog gene of the present invention serves to improve the sensitivity of a cell to an anticancer agent comprising the above-mentioned DNA-damaging factor by expressing its antisense strand in a tumor tissue to specifically control its gene product. Therefore, the mutant Rad51 paralog gene can be expected to be used as an agent for gene therapy, wherein the agent exhibits an anticancer action.

2. Mutant Rad51 Paralog Peptide of the Present Invention

There can be provided a mutant Rad51 paralog peptide by the above-mentioned mutant Rad51 paralog gene. The mutant Rad51 paralog peptide is also encompassed in the scope of the present invention. The mutant paralog peptide also includes a peptide having mutations in Walker motif, which is an active center of ATP hydrolyzing activity. By the mutations in this motif, there can be prepared a mutant paralog peptide having dominant negative activity.

The mutant Rad51 paralog peptide of the present invention includes a gene encoded by the above-mentioned mutant Rad51 paralog gene. Further, the mutant Rad51 paralog peptide of the present invention includes a mutant Rad51 paralog peptide having substitution, deletion, insertion or addition of at least one amino acid residue in an amino acid sequence selected from the group consisting of SEQ ID NOs: 2, 4 and 6, wherein the mutant Rad51 paralog peptide shows an activity for enhancing sensitivity of a cell to a DNA-damaging factor.

Here, the amino acid sequences of SEQ ID NOs: 2, 4 and 6 mentioned above show the sequences of Rad51B, Rad51C, and Rad51D, respectively.

Concretely, the above-mentioned mutant Rad51 paralog peptide includes a peptide having an amino acid sequence selected from the group consisting of:

(i) an amino acid sequence in which a region of 137th to 173rd amino acids is deleted or substituted with a sequence of a marker peptide in the amino acid sequence of SEQ ID NO: 2;

(ii) an amino acid sequence in which a region of 196th to 235th amino acids is deleted or substituted with a sequence of a marker peptide in the amino acid sequence of SEQ ID NO: 4; and (iii) an amino acid sequence in which a region of 138th to 153rd amino acids is deleted or substituted with a sequence of a marker peptide in the amino acid sequence of SEQ ID NO: 6.

When the mutant Rad51 paralog peptide, especially Rad51B mutant peptide, Rad51C mutant peptide or Rad51D mutant peptide, is expressed in a cell, there is exhibited an excellent characteristic that the mutant peptide has a high specificity to cisplatin as compared to that of a known Rad51 mutant peptide.

The "activity for enhancing sensitivity of a cell to a DNA-damaging factor" can be evaluated as described in, for instance, Example 3.

Since the mutant Rad51 paralog peptide of the present invention shows an activity for enhancing sensitivity of a cell to a DNA-damaging factor, the mutant Rad51 paralog peptide is useful as a target for an anticancer agent comprising a DNA-damaging factor. Accordingly, there is expected its application as an anticancer agent in combined use with the anticancer agent comprising a DNA-damaging factor.

Also, in the mutant Rad51 paralog peptide of the present invention, the encoded protein shows an activity for enhancing sensitivity of a cell to a DNA-damaging factor, and especially its homologous recombination repair capacity is lowered or diminished. Therefore, when a DNA-damaging factor, for instance, cisplatin, mitomycin C or the like, is used as an anticancer agent, the mutant Rad51 paralog peptide is especially useful for an application to a screening of a drug having a higher anticancer action.

3. Transformed Cell of the Present Invention

According to the mutant Rad51 paralog gene of the present invention, there is provided a transformed cell having the gene. The transformed cell is also encompassed in the scope of the present invention. Since the transformed cell of the present invention has the above-mentioned mutant Rad51 paralog gene, the sensitivity of a cell to a DNA-damaging factor is further enhanced as compared to a normal cell. Therefore, the transformed cell is useful for screening a drug having a DNA cross-linking ability comparable to cisplatin or the like.

The transformed cell of the present invention can be obtained by introducing the mutant Rad51 paralog gene of (1) mentioned above into a host cell.

A subject for a host cell is not only DT40 cell but also all the human cell lines. Among them, the above-mentioned DT40 cell is an excellent model for detailed functional analyses of Rad5 paralog because the DT40 cells have more efficient homologous recombination repair capacity than that of mammalian cells [Buerstedde, J. M. et al., Cell, 67, 179–188 (1991)], and gene targeting therefor is easy.

A means for introducing a gene into a host cell includes, for instance, calcium phosphate method, lipofection method, electroporation method and the like. When a gene is introduced into a host cell, there may be used a recombinant vector resulting from incorporation of a mutant Rad51 paralog gene into a vector depending upon the host cell used.

In a case where a marker gene exists on the mutant Rad51 paralog gene, the transformed cell can be sorted out by using the expression of the marker gene as an index. Also, in a case where a vector is used when a gene is introduced into a host cell, the transformed cell can be sorted out by using expression of the marker gene on the vector as an index.

As to the culture of the transformed cell, appropriate conditions can be set depending upon the host cell. The culture conditions for the transformed cell are not special ones, and are as follows: incubation in a Dulbecco's liquid medium containing an antibiotic, fetal bovine serum and avian serum with an incubator at 5% $CO_2$ and 37° C.

In the present specification, the transformed cells deficient in each gene of the above-mentioned Rad51B, Rad51C and Rad51D are referred to rad51b cell, rad51c cell, rad51d cell, respectively.

4. Screening Method of the Present Invention

According to the above-mentioned transformed cell, there can be performed screening of a drug having a DNA-damaging action. The present invention also encompasses the screening method.

The screening method of a drug having a DNA-damaging action of the present invention comprises the steps of:

(1) contacting a test substance with the above-mentioned transformed cell; and (2) evaluating a response of the cell obtained in the step (1).

In the screening method, the transformed cell having sensitivity of a cell to a DNA-damaging factor. Therefore, according to the method, there is exhibited an excellent effect such that a drug having a DNA-cross-linking ability comparable to cisplatin or the like can be screened.

The test substance includes a compound, a peptide, an extract and the like as desired.

In the step (1), the contact of the test substance with the transformed cell can be carried out by adding a test substance to a medium of the transformed cell so as to have an appropriate concentration, and culturing the transformed cell. The culture conditions can be appropriately set depending upon the transformed cell.

In the step (2), the response of the cell can be evaluated by using viability of the cell, chromosomal breakages, homologous recombination (targeted integration frequency) on the chromosomes, sister chromatid exchange, and the like as an index.

For instance, when in the transformed cell in the presence of a test substance, the level of the chromosomal breakages has been increased, the homologous recombination (targeted integration frequency) on the chromosomes has been lowered, and the level of the sister chromatid exchange is lowered, as compared to those in the absence of the test substance, the test substance can serve as an index of a drug having DNA-damaging action. Also, in an appropriate host cell, the accuracy of the screening can be further increased by carrying out the same procedures as the evaluation in the transformed cell.

5. Screening Method for DNA Repair Controlling Agent

According to the findings of the present inventors, there can be further provided a screening method for a DNA repair inhibitor.

According to the findings of the present inventors, since Rad51 paralogs, especially Rad51B, Rad51C and Rad51D, are deeply involved in the homologous recombination repair, a controlling agent for DNA repair can be screened by evaluating the increase or decrease, or presence or absence of the function of normal Rad51B, Rad51C or Rad51D. In addition, the above-mentioned Rad51B, Rad51C and Rad51D have an excellent characteristic of high specificity to cisplatin when the above-mentioned Rad51B, Rad51C and Rad51D are expressed in the cell, as compared to a known Rad51.

Concretely, the screening method for a controlling agent for DNA repair of the present invention comprises the steps of:

(I) contacting a test substance with a transformed cell having a nucleic acid having (A) a nucleotide sequence selected from the group consisting of SEQ ID NOs:1, 3 and 5; or (B) a nucleotide sequence different from the nucleic acid of the (A) mentioned above via degeneracy; and (II) evaluating a homologous recombination repair capacity in the cell.

The transformed cell having a nucleic acid having the (A) or (B) mentioned above can be prepared by the same technique as that for the transformed cell described in section 3. above. For instance, a transformed cell can be obtained by incorporating a nucleic acid having the (A) or (B) mentioned above into an appropriate vector, and introducing the resulting recombinant vector into an appropriate host.

In the step (I), the contact of the test substance with the transformed cell can be carried out by adding a test substance to a medium of the transformed cell so as to have an appropriate concentration, and culturing the transformed cell. The culture conditions can be appropriately set depending upon the transformed cell.

In the step (II), the homologous recombination repair capacity can be evaluated by using chromosomal breakages, homologous recombination (targeted integration frequency) on the chromosomes, sister chromatid exchange, and the like as an index. For instance, the homologous recombination repair capacity can be evaluated by the analysis of sister chromatid exchange, the analysis of the targeted integration frequency and the like as described in Example 2.

As to the index showing that the test substance is a controlling agent for DNA repair, in the transformed cell in the presence of a test substance, when the homologous recombination (targeted integration frequency) on the chromosomes is lowered, and the level of the sister chromatid exchange is lowered, as compared to those in the absence of the test substance, the test substance can serve as an index of having DNA repair-suppressing capacity. On the other hand, in the transformed cell in the presence of a test substance, when the homologous recombination (targeted integration frequency) on the chromosomes is increased, and the level of the sister chromatid exchange is increased, as compared to those in the absence of the test substance, the test substance can serve as an index of having DNA repair-enhancing capacity. Also, in an appropriate host cell, the accuracy of the screening can be further increased by carrying out the same procedures as the evaluation in the transformed cell.

The controlling agent for DNA repair obtained by the screening method can be utilized for controlling the DNA repair capacity. Concretely, in a case of a drug that lowers a DNA repair capacity, the drug for enhancing sensitivity of a cell to a DNA-damaging factor can be administered in combination with an anticancer agent having a DNA-damaging action, represented by cisplatin, mitomycin C.

The present invention will be described in further detail by means of Examples, without intending to limit the present invention to these Examples.

EXAMPLE 1

Involvement of rad51 Gene in Cell Growth (1) Preparation of rad51 Gene Targeting Construct Each of Rad51 paralog defective mutant clones (rad51c mutant, rad51d mutant, xrcc2 mutant and xrcc3 mutant) shown in the panel (B) of FIG. 1 were prepared from avian cell line DT40 [the above-mentioned Buerstedde et al. (1991)] as described below.

Genomic DNA fragments of the Rad51-related genes were isolated from DT40 genomic DNA by long-range PCR with primers based on cDNA sequences. Next, the gene targeting constructs were prepared in accordance with the description of the above-mentioned Buerstedde et al. (1991) as follows: Concretely, both of two kinds (both sides) of several-kb genomic DNA fragments on both sides of the genomic DNA of the region to be disrupted, which were isolated by the above-mentioned long-range PCR were cloned in an appropriate vector. Next, a plasmid in which a selection marker was inserted between the two kinds of the DNAs was prepared. Thereafter, a DNA resulting from cleavage of the vector-derived portion in the above-mentioned plasmid was introduced into DT40 cells by electroporation using the resulting DNA as a gene targeting construct.

Regarding these constructs, gene targeting was performed so that an amino acid sequence corresponding to each of the published human genes: 196th to 235th amino acids in Rad51C [the above-mentioned Dosanjh et al. (1998); GenBank Accession NO: AF029669], 138th to 153rd amino acids in Rad51D [Cartwright, R. et al., *Nucleic Acids Res.*, 26, 1633–1659 (1998); GenBank Accession NO: AF034956], 47th to 89th amino acids in XRCC2 [the above-mentioned Liu et al. (1998); GenBank Accession NO: AF035587], and 212th to 242nd amino acids in XRCC3 [the above-mentioned Tebbs et al. (1995); GenBank Accession NO: AF035586] was substituted with a selection marker (puromycin resistance gene or the like).

Next, the human Rad51 and Rad51 paralogs were incorporated into an expression vector prepared on the basis of expression vector pAGS3 carrying the avian β-actin promoter (prepared by Professor Kurasaki of Osaka University, Faculty of Medicine), to give a recombinant vector. The resulting recombinant vector was transfected into DT40 cell line. The DNA transfection was carried out in accordance with the conditions as described in the above-mentioned Buerstedde et al. (1991). Concretely, the DNA transfection was carried out under the conditions such that 50 μg of a gene targeting construct DNA was placed in PBS(−), that $10^7$ cells were suspended in 0.8 ml of the above-mentioned solution [PBS(−)], that the suspension was set in Gene pulser of Bio-Rad, and that electric pulses were applied to the cells at 25 μF and 550 V.

(2) Culture of Mutant Clones

For the mutant clone obtained in (1) above, the cell culture was carried out in accordance with the conditions as described in Buerstedde et al. (1991), supra. Concretely, the cell culture was carried out on a culture plate using Dulbecco's minimum essential medium [manufactured by Gibco-BRL] under the conditions of 5% $CO_2$, 20% $O_2$ atmosphere. The cells were maintained at a density of $10^3$ cells/ml to $10^6$ cells/ml, and the exchange of the media and the dilution of the cells (with a fresh medium) were carried out once in two days.

As a result, as is observed in rad51b (indicated by RAD51B-/-) mutant, the proliferation rates of rad51c mutant, rad51d mutant, xrcc2 mutant and xrcc3 mutant were significantly lower than that of wild-type cells. While the length of the cell cycle is comparable between wild-type and mutant clones, higher proportions of dead cells were seen in these mutant clone cultures as shown in FIG. 1. Therefore, it was demonstrated that the rad51 mutant clones showed slower growth rates.

EXAMPLE 2

Chromosome Analysis (1) Chromosome Analysis

In order to investigate the cause of cell death, chromosome analysis of metaphase-arrested cells was performed. The results are shown in Table 1.

TABLE 1

Spontaneous Chromosomal Aberrations

| Genotypes of Cells Analyzed | Chromosome-type | | Chromatid-type | | Total | Total |
|---|---|---|---|---|---|---|
| | Breakages | Gaps | Breakages | Gaps | Breakages + Gaps | Breakages |
| Wild-type | 0.25 | 0.25 | 0.25 | 1.25 | 2 ± 0.7 | 0.5 ± 0.5 |
| rad51c | 0 | 6 | 6.7 | 3.3 | 16.0 ± 3.3 | 6.7 ± 2.1 |
| rad51d | 14 | 8.7 | 10 | 6 | 38.7 ± 5.1 | 24 ± 4.0 |
| xrcc2 | 0 | 9.3 | 6.7 | 5.3 | 21.0 ± 3.8 | 6.7 ± 2.1 |
| xrcc3 | 2.7 | 10.7 | 6.7 | 6 | 26.0 ± 4.2 | 9.4 ± 2.5 |

In Table 1, data are presented as the number of aberrations per 100 cells. At least 150 mitotic cells were analyzed for each genotype. Total aberrations per cell and SE were calculated as follows: Concretely, the cells are treated with colcemid for 3 hours, and then fixed. On the following day, the fixed cells are fixed on a slide glass and then stained. One-hundred or more cells in which the number of chromosomes is normal and the chromosomes are condensed were analyzed, and the number of chromosomal breakages was counted.

It is found from the results of Table 1 that in the four kinds of the mutant clones, the levels of spontaneous chromosomal breakages, which are causative for the reduced viability, are significantly increased. These findings are considerably consistent with those for rad51b DT40 cells, and qualitatively similar to those for XRCC2-deficient hamster cells and XRCC3-deficient hamster cells [the above-mentioned Tebbs et al. (1995); the above-mentioned Cartwright et al., *Nucleic Acids Res.*, 26, 3084–3089 (1998); the above-mentioned Liu et al. (1998)].

The spontaneous chromosomal aberrations in each of these mutant clone cultures obtained in Example 1 mentioned above could be caused by defective homologous recombination repair of replication-associated double-strand DNA breakages [the above-mentioned Haber (1999)]. In order to evaluate the homologous recombination capacity of each mutant, both the efficiency of targeted integration of transfected genomic DNA fragments and the level of sister chromatid exchange were determined.

(2) Determination of Targeted Integration Frequencies

In order to analyze targeted integration events at the β-actin, ovalbumin [the above-mentioned Buerstedde et al. (1991)] and XRCC2 loci, Southern blot analysis was carried out for each of the mutant clones obtained in Example 1 mentioned above.

The gene targeting construct obtained in the Example 1 mentioned above was transfected into the wild-type DT40 cells and each mutant cell, and a clone resistant to an appropriate antibiotic was sorted out. Each of chromosomal DNAs was isolated from each of the resulting clones by a conventional method. Next, Southern blot analysis was carried out for each of the chromosomal DNA using a DNA fragment (a size of up to 1 kb) just near the gene targeting construct in each locus as a probe. The hybridization conditions were ordinary conditions, i.e. hybridization: 65° C., 1 M NaCl, 50 mM Tris-HCl (pH 7.4), 0.5% SDS, Denhardt's solution, denatured salmon sperm DNA (10 μg/ml); washing: 65° C., 0.3×SSC, 0.1% SDS.

Thereafter, the targeted integration frequency was evaluated by the following formula:

[the number of colonies showing a band having a pattern different from the band of the parent strain, each of the bands being shown by Southern blotting]/[the number of total drug resistance colonies analyzed]

The results are shown in Table 2.

TABLE 2

Targeted Integration Frequencies

| | Targeting Constructs | | | |
|---|---|---|---|---|
| Genotype | XRCC2-puro | *Ov-puro | *Ov-neo | KU70-hyg |
| Wild-type | 12/20 (60%) | 24/37 (65%) | 18/36 (50%) | 11/18 (61%) |
| rad51c | 2/48 (4.2%) | 5/46 (11%) | ND | ND |
| rad51d | 0/38 | 0/22 | ND | ND |
| xrcc2 | ND | ND | 0/34 | 0/43 |
| xrcc3 | 0/42 | 0/36 | ND | ND |

In the table, data show the number of targeted clones in each locus per number of drug resistance clones analyzed. Also, in the table, the ratio of targeted integration events is given in parenthesis. Further, in the table, two targeting constructs of the ovalbumin locus comprise either a puromycin resistance gene or a neomycin resistance gene. ND means not determinable.

As shown in Table 2, the targeted integration frequencies were reduced by about 8-fold in the rad51c clone and by at least 30-fold in the rad51d clone, the xrcc2 clone and the xrcc3 clone.

(3) Analyses of Chromosome Aberrations and Sister Chromatid Exchange

Analyses of chromosome and sister chromatid exchange were carried out in accordance with the descriptions given in the above-mentioned Sonoda et al. (1998) and the above-mentioned Sonoda et al. (1999). Concretely, living cells are cultured in the presence of BrdU for double cell division cycles. After performing the manipulation of rupture and fixation of the cells by hypotonic fixation, the cells (chromosomes) are fixed on a slide glass. The fixed cells are irradiated with ultraviolet rays to break genomic DNA resulting from incorporation of BrdU into both the double strand. The protein adherent to the broken DNA is washed away, and the remaining chromatin protein adherent to genomic DNA is stained.

In order to analyze MMC-inducing sister chromatid exchanges, cells were incubated in a medium containing 0.05 μg/ml MMC in an atmosphere of 5% $CO_2$ and 20% $O_2$, at humidity of 100%, and at 39.5° C. (or may be 37° C.) for 12 hours (the length of the cell cycle of DT40 cells being about 8 hours). Colcemid (N-deacetyl-N-methylcolchicine) was added in a concentration of 0.1 mg/ml at a point 1.5 hours before the harvest of the cells, and the mixture was further incubated. The results for each of the sister chromatid exchanges are shown in FIG. 2.

Figure 2:
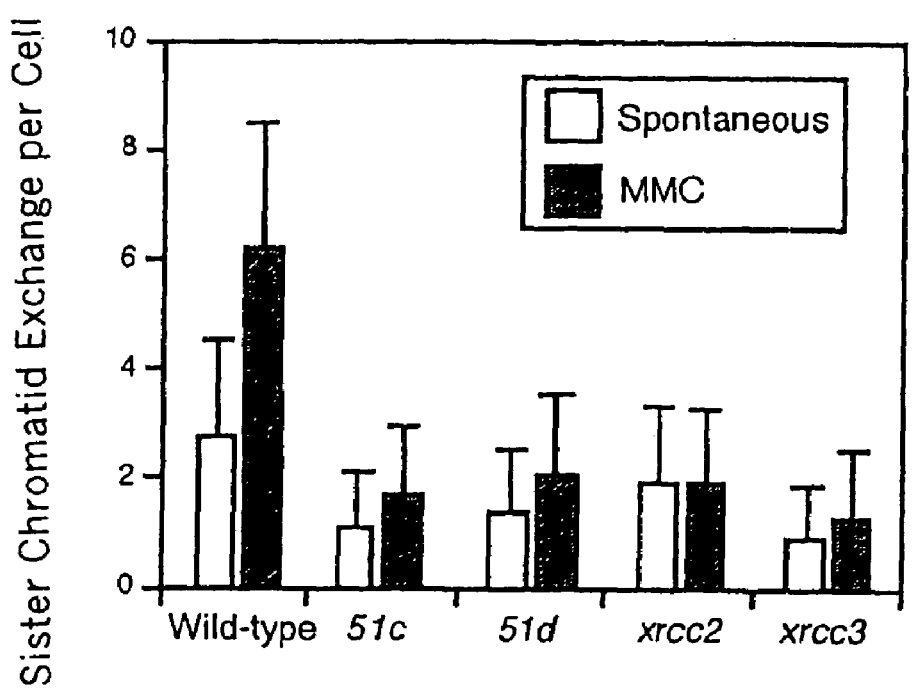
FIG. 2 is a diagram showing the levels of sister chromatid exchange per cell before and after MMC treatment. One-hundred and fifty cells were analyzed in each preparation. Error bars represent SD.

It is seen from FIG. 2 that the Rad51-paralog mutants exhibit significantly reduced levels of both the spontaneous sister chromatid exchanges as well as the sister chromatid exchanges induced by mitomycin C (MMC), a cross-linking agent. Also, the present inventors have previously shown that the sister chromatid exchange events would reflect post-replicational repair by homologous recombination that is probably associated with crossing-over between sister duplexes [the above-mentioned Sonoda et al. (1999)]. These findings suggest that each paralog is actually involved in the homologous recombination.

EXAMPLE 3

(1) Sensitivity of Cells Against DNA-Damaging Factors (γ-Rays, MMC and Cisplatin)

Cells which were serially diluted ($10^2 \times 10$ cells/µl, $10^3 \times 10$ cells/µl, $10^4 \times 10$ cells/µl and $10^5 \times 10$ cells/µl) were plated on a plate of methyl cellulose-containing medium [composition: Dulbecco's medium, fetal bovine serum (15%), chicken serum (1.5%), methyl cellulose (15 g/l)], and cultured in an atmosphere of 5% $CO_2$ and 20% $O_2$, at humidity of 100%, and 39° C. Next, $^{137}$Cs γ-ray source was irradiated to the plate for 30 to 90 seconds. Further, the cells were cultured in an atmosphere of 5% $CO_2$ and 20% $O_2$, at humidity of 100%, and 39° C. for one week. Thereafter, colony survival assay was carried out using the number of colonies on a plate without subjected to γ-ray irradiation as control, thereby evaluating sensitivity of the cells to γ-ray irradiation.

In addition, the cells were incubated in a complete medium containing MMC (manufactured by KYOWA HAKKO KOGYO CO., LTD.) at 39° C. for 1 hour, and washed with a warm medium at 37° C. thrice. The washed cells were then plated on the above-mentioned methyl cellulose-containing medium. The cells were cultured in an atmosphere of 5% $CO_2$ and 20% $O_2$, at humidity of 100%, and 39° C. Thereafter, the colony survival assay was carried out using the number of colonies appearing on the plate on which the cells untreated with MMC were plated as control, thereby evaluating sensitivity of the cells to MMC.

Further, the cells were plated on a plate of methyl cellulose containing cisplatin (manufactured by NIPPON KAYAKU CO., LTD.), and cultured in an atmosphere of 5% $CO_2$ and 20% $O_2$, at humidity of 100%, and 39° C. Thereafter, the colony survival assay was carried out, thereby evaluating sensitivity of the cells to cisplatin.

The biologically associated DNA repair capacity of each mutant was evaluated in colony survival assays after exposure to a DNA-damaging factor. As a result, clearly, rad51c mutant, rad51d mutant, xrcc2 mutant and xrcc3 mutant all showed a very similar pattern of sensitivities, which were also consistent with those of rad51b cells. As shown in the panel (A) of FIG. 3, the γ-ray sensitivity of each mutant was mild, each of which was about 3-fold sensitive to MMC than that of the wild-type DT40 cells, based on estimated D10 values.

Figure 3:
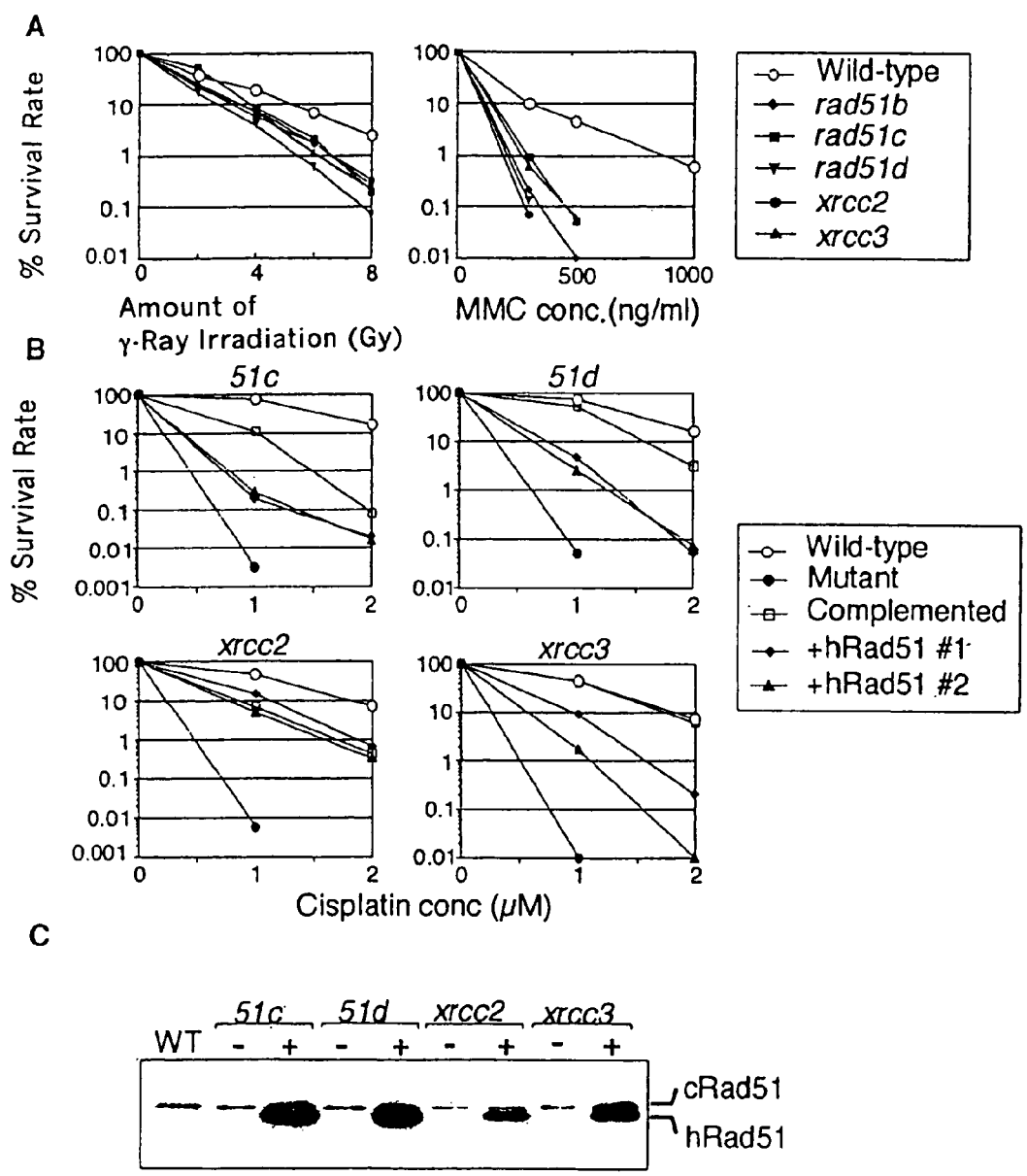
FIG. 3 are graphs each showing the sensitivity of knock-out cell lines to DNA-damaging factors. The panel (A) shows survival curves after treatments with γ-ray irradiation and MMC. Sensitivity data of rad54 and rad51b cells were previously described (Tanaka et al., submitted). The panel (B) shows partial enhancement of cisplatin sensitivity in knockout mutants by overexpression of human Rad51. Data shown are representative of at least two independent experiments. The panel (C) shows the results of Western blot analysis of human Rad51 transformants derived from knockout mutants. The transformants have much higher steady-state levels of cDNA-derived human Rad51 than endogenous Rad51.

However, as shown in the panel (B) of FIG. 3, each mutant was about 8-fold more sensitive than normal cells to killing by cisplatin (cis-diamminedichloroplatinum-II), a DNA cross-linking agent that has been widely used in chemotherapy. The complementation of these mutants with human cDNAs corresponding to mutant genes in these mutants restored their cisplatin sensitivity to nearly normal levels.

From these results, it is confirmed that the rad51 paralog gene disruptions were causation for the increased sensitivity to cisplatin. It should be noted that the previous findings on XRCC2 and XRCC3 mutant hamster cells [the above mentioned Tebbs et al. (1995); the above mentioned Liu et al. (1998)] are considerably consistent with the new corresponding DT40 mutants of the present inventors for all properties examined (mild radiosensitivity, high sensitivity to cross-linking agents, chromosomal instability, and defective homologous recombination) except that the mutant hamster cells showed more pronounced sensitivity to MMC, i.e., only a few-fold sensitive to γ-rays while 60 to 70-fold sensitive to MMC based on estimated D10 values [the above-mentioned Thompson et al. (1999)]. Accordingly, the role of the Rad51 paralogs in the homologous recombination repair is likely to be conserved between DT40 and mammalian cells.

(2) Phenotypic Suppression of Rad51-Paralog Mutants by Rad51 Overexpression

In yeast, it has been shown that the overexpression of Rad51 partially suppresses the ionizing radiation sensitivity of rad55 and rad57 mutant strains [the above-mentioned Hays et al. (1995); the above-mentioned Johnson et al. (1995)]. Furthermore, it has been shown that the overexpression of human Rad51 cDNA in rad51b cells also restores the sensitivity to γ-rays and MMC (but not restoring to cisplatin) to wild-type levels.

Similar to these, as shown in the panel (B) of FIG. 3, Rad51 overexpression partially complements the sensitivities of each of rad51c mutant, rad51d mutant, xrcc2 mutant and xrcc3 mutant to cisplatin. Accordingly, it is seen that human Rad51 at least partially complements for each of these paralogs under conditions where the amount of human Rad51 protein is highly overexpressed as compared with the endogenous Rad51 level [the panel (C) of FIG. 3].

EXAMPLE 4

Analysis of Nuclear Rad51 Focus Formation

In order to further evaluate the role of the paralogs in the homologous recombination, the nuclear Rad51 focus formation was analyzed by γ-ray irradiation.

Foci that can be microscopically confirmed show an assembly of Rad51 into atypically long nucleoprotein filaments probably involved in homologous recombination repair [the above-mentioned Bishop et al. (1998); Raderschall, E. et al., *Proc. Natl. Acad. Sci. USA*, 96, 1921–1926 (1999)].

Therefore, wild-type and mutant cultures with progressing cell cycles were exposed to γ-rays and MMC, and thereafter the cells were immunostained with anti-Rad51 antiserum. The results are shown in FIG. 4.

Figure 4:
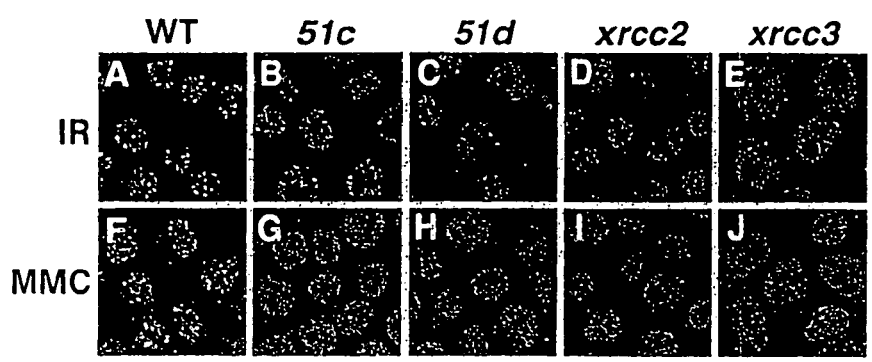
FIG. 4 is a photograph showing the results of induction of Rad51 foci by genotoxic treatments. Immunofluorescence of Rad51 nuclear foci after γ-ray irradiation (8 Gy) (A to E) or MMC treatment (500 ng/ml, 1 hour) (F to J) was visualized as previously described [Yamaguchi-Iwai et al. (1998)]. In the figure, A and F are wild-type; B and G are rad51c; C and H are rad51d; D and I are xrcc2; E and J are xrcc3, respectively.

It is seen from FIG. 4 that the formation of Rad51 foci was severely impaired in each mutant cell line after ionizing radiation and MMC treatments, as previously observed in XRCC3-deficient hamster cells [the above-mentioned Bishop et al. (1998)]. After five hours of the ionizing radiation or MMC treatment, less than 15% of the mutant cells contained a significant number of distinct Rad51 foci (exceeding 4 per cell), whereas more than 60% of wild-type cells showed robust formation of the foci. Since protein levels of Rad51 did not change after genotoxic treatment in any mutant clone (data not shown), these results show that all Rad51 paralogs are required for damage-induced redistribution of Rad51 within the nucleus. In the absence of each of these five kinds of the paralog proteins, there must still be a basal level of Rad51 activity since the mutants are viable. Accordingly, these five kinds of the proteins are required in the formation of very long-track Rad51 filaments, which are microscopically visible.

The reconstruction of Rad51 focus formation could not be evaluated because of high background level of immunostaining in the presence of overexpressed human Rad51 protein. These data combined with the defective Rad51 focus formation in every Rad51-paralog mutant suggest that all these proteins are involved in the recruitment of Rad51 into nucleoprotein filaments that mediate homologous pairing and exchange.

INDUSTRIAL APPLICABILITY

According to the present invention, there is enabled a screening of a novel anticancer agent which allows a more efficient therapy for a cancer, wherein the agent is an agent capable of enhancing the sensitivity of a cell to an anticancer agent comprising a DNA-damaging factor or an agent having a DNA-damaging action.

The invention claimed is:

1. An isolated human mutant Rad51 paralog nucleic acid molecule comprising SEQ ID NO: 1, except that nucleotides 463–573 of SEQ ID NO: 1 are deleted or substituted with a marker gene, wherein the marker gene is selected from the group consisting of puromycin resistance gene, histidinol resistance gene, Ecogpt gene, blastocitidin resistance gene and hygromycin resistance gene.

2. The isolated human mutant Rad51 paralog nucleic acid molecule according to claim 1, wherein a protein encoded thereby shows an activity for enhancing sensitivity of a cell to a DNA damaging factor, and wherein the DNA-damaging factor is selected from one or more of the group consisting of: irradiation rays, mitomycin C and cisplatin.

3. An isolated transformed cell having the nucleic acid molecule of claim 1.

4. The isolated transformed cell according to claim 3, wherein the cell is DT40.

5. A screening method for a test substance having DNA damaging action comprising the steps of:
  a) contacting a test substance with the transformed cell of claim 3 or 4; and
  b) evaluating a response of the cell obtained in step a), wherein the response of the cell is evaluated by analyzing cell growth rate, chromosomal breakages, homologous recombination, or sister chromatid exchange as an indicator of DNA damaging action of the test substance.

* * * * *